| United States Patent [19] | [11] 3,959,468 |
| Burmeister | [45] May 25, 1976 |

[54] ANTIBIOTIC EQUISETIN AND METHOD OF PRODUCTION

[75] Inventor: Harland R. Burmeister, Peoria, Ill.

[73] Assignee: The United States of America as represented by the Secretary of Agriculture, Washington, D.C.

[22] Filed: May 6, 1974

[21] Appl. No.: 467,548

[52] U.S. Cl. .................................. 424/122; 195/81
[51] Int. Cl.² ........................................ A61K 35/00
[58] Field of Search ........................ 195/81; 424/122

[56] References Cited
UNITED STATES PATENTS

| 3,737,523 | 6/1973 | Cole et al. ........................... 424/122 |
| 3,793,449 | 2/1974 | Cole et al. ........................... 424/122 |

*Primary Examiner*—Jerome D. Goldberg
*Attorney, Agent, or Firm*—M. Howard Silverstein; Max D. Hensley; David G. McConnell

[57] ABSTRACT

An antibiotic produced by *Fusarium equiseti* NRRL 5537 and given the trivial name equisetin is active against several genera of gram-positive bacteria.

4 Claims, 3 Drawing Figures

ANTIBIOTIC EQUISETIN AND METHOD OF PRODUCTION

BACKGROUND OF THE INVENTION

The invention relates to a new antibiotic. More specifically, it relates to the antibiotic equisetin produced by *Fusarium equiseti* NRRL 5537.

It is known that various species of Fursarium produce toxins which are implicated in mycotoxicoses in several areas of the world. Burmeister et al. [Appl. Microbiol. 23: 1165–1166 (1972)] incubated 136 strains of Fusarium sp. to determine their capacity to produce T-2 toxin.

The inventor has now discovered that one strain, *F. equiseti* NRRL 5337, produces a substance that strongly inhibits several genera of gram-positive bacteria.

Although many antibiotics and mycotoxins are produced by strains of Fusarium species, none have the biological activity and the chemical properties of the antibiotic elaborated by *F equiseti* NRRL 5537. The principal fusariotoxins: zearalenone [Mirocha et al., *Microbial Toxins*, Vol. 7, Kadis, Ciegler, and Ajl (ed.), Academic Press, Inc., New York, 1971, pp. 107–138], butenolide [Yates et al., J. Agr. Food Chem. 17: 437–442 (1969)], fusariogenin [Joffe, A. Z., *Microbial Toxins*, Vol. 7, supra, pp. 139–189], or the 12,13-epoxytrichothecenes [Bamburg et al., *Microbial Toxins, Vol. 7*, supra, pp. 207–292] either lack or only exhibit weak antibacterial properties. Of the antibacterial metabolites produced by the genus Fusarium, the enniatins [Korzybski et al., *Antibiotics: Origin, Nature and Properties*, Vol. 2, Pergamon Press, Oxford, England, 1967, pp. 1310–1325] are most nearly like the antibiotic of *F. equiseti* NRRL 5537 in their microorganism-inhibition spectrum. Both the enniatins and the product of *F. Equiseti* NRRL 5537 inhibited *Mycobacterium pheli*, *Bacillus subtilis*, and *Staphylococcus aureus in vitro* at concentratons below 1 $\mu$g./ml. However, the enniatins and equisetin are grossly different in their chemical and physical properties.

The drawings consist of three figures showing infrared (IR), ultraviolet (UV), and mass spectrographic spectra of equisetin.

DETAILED DESCRIPTION OF THE INVENTION

Figure 1:
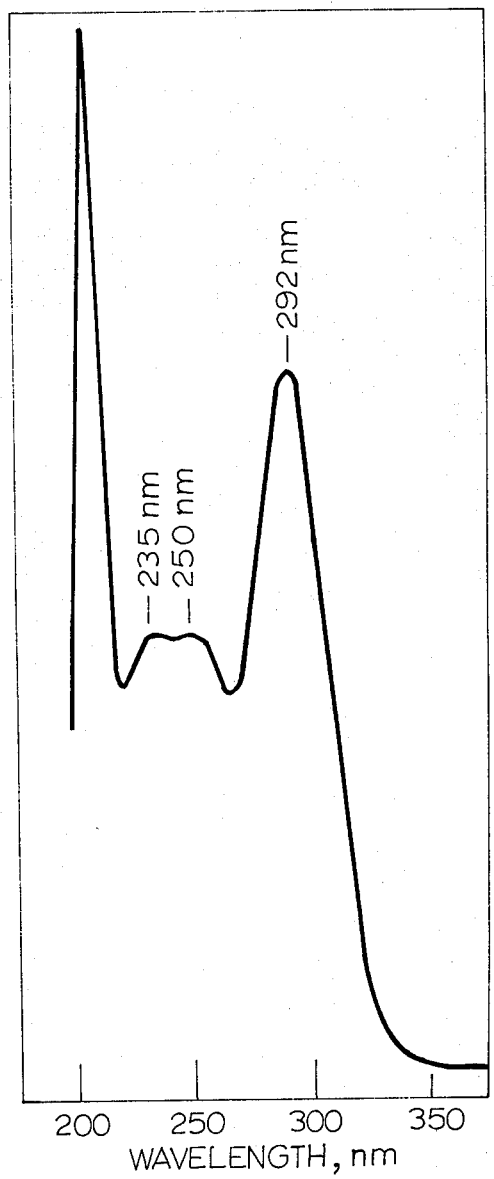

The fungus strain NRRL 5537 of *Fusarium equiseti* employed in this process was isolated from a sample of fescue hay, and a specimen of the strain has been deposited with the ARS Culture Collection, United States Department of Agriculture (Northern Regional Research Center), Peoria, Illinois, U.S.A., where it is permanently available to the public under the reference NRRL 5537.

The new strain NRRL 5537 of the fungus species *Fusarium equiseti* grows on glucose/malt extract/yeast extract/peptone agar at 15° to 25° C. and forms a white, low aerial mycelium. The under side of the colony shows a yellow-brown coloration of the substrate. On white corn grits moistened to contain about 30% water, the fungus NRRL 5537 forms a white, low aerial mycelium bearing copious amounts of conidia typical of the fungus *F. equiseti*. The under side of the colony shows a pink to red coloration of the substrate.

Morphologically and physiologically the new strain NRRL 5537 corresponds to the description of the fungus species *Fusarium equiseti* by C. Booth [*The Genus Fusarium*, Commonwealth Mycological Institute, Surrey, England, 1971, pp. 157–159].

The new strain NRRL 5537 of the fungus species *Fusarium equiseti* may be cultivated on various media containing the usual nutrients to provide the new antibiotic. For example, nutrients usually employed for carbon-heterotrophic organisms may be used. For example, glucose, starch, dextrin, or cane sugar may be used as the carbon source; organic and inorganic nitrogen-containing compounds, such as peptone, yeast or meat extracts, ammonium sulfate, ammonium nitrate or amino acids may be used as the nitrogen source, as well as the usual mineral salts and trace elements. The new strain also can be cultivated on numerous moist natural products to provide the new antibiotic. For example, white corn grits, cracked corn, pearled wheat, or rolled oats.

One method of producing the antibiotic equisetin comprises inoculating a moistened white corn grit medium with a conidial suspension of the new strain of *Fusarium equiseti* and incubating at 20° C. for 21 da. The cultivation may be effected under aerobic conditions by static surface culture fermentation or by a process whereby the culture is continually mixed by shaking. As soon as the maximum amount of antibiotic is produced, the culture is extracted with a suitable solvent.

One convenient method of isolating the antibiotic of the present invention comprises extraction of the culture with acetone, although other solvents, e.g., chloroform, ethyl acetate, methanol, or benzene may likewise be used. The new antibiotic may be isolated from the crude extract by chromatography or partitioning between suitable solvent, e.g., hexane and methanol.

The primary recovery of the antibiotic from 16–25 g. of crude product yielded 0.48–1.3 g. of a white powder. When chromatogrammed, the purified antibiotic was colorless and nonfluorescent; it appeared as a single spot on thin layer chromatographic (TLC) plates developed with either acetonitrile-water-benzene (90:6:4, v/v/v, $R_F$ 0.53) or toluene-methanol (7:3, v/v, $R_F$ 0.61). In light, equisetin was visible as a reddish spot after spraying with p-anisaldehyde reagent and heating to 110° C. for 5–10 min. The antibiotic gave a positive ferric chloride test. Exposure of chromatograms to iodine vapor or spraying with concentrated sulfuric acid revealed no additional zones.

The white amphorous powder has a melting range of 65°–66° C. It was soluble in acetone (>660 mg./ml.), ethanol (>330 mg./ml.), and methanol (>220 mg./ml.); insoluble in hexane (<0.8 mg./ml.); and water (<0.3 mg./ml.). The UV spectrum of equisetin in ethanol is reproduced in FIG. 1. Absorption maxima occurred at 292 ($\epsilon = 10,760$), 250, and 235 nm. The minor peaks at 250 and 235 nm. are of equal intensities.

Elemental analysis [C, 70.95; H, 8.39; N, 3.14, 0, 17.52 (by difference)] and the molecular ion peak of $m/e = 373$ obtained by high resolution mass spectroscopy of equisetin (FIG. 2) correspond to a formula of $C_{22}H_{31}NO_4$. The green copper salt prepared from equisetin had a melting range of 180°–190° C. This product yielded analytical values in accord with the copper salt of a compound having the formula $C_{22}H_{31}NO_4$. [Found on material dried at 100° C. in a high vacuum: C, 64.64; H, 7.15; N, 3.50; Cu, 7.85. Cu $(C_{22}H_{30}NO_4)_2$ ½ $H_2O$ requires: C, 64.58; H, 7.17; N, 3.42; Cu, 7.77.[

Figure 3:
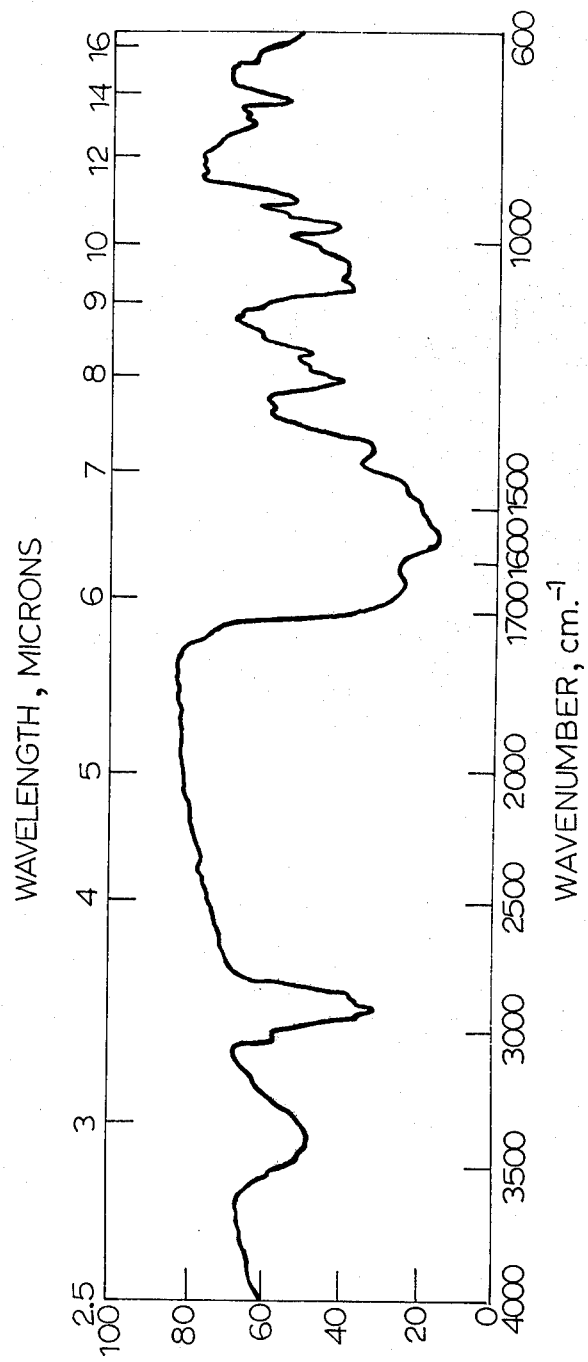

The IR spectrum of equisetin on a KRS-5 plate is shown in FIG. 3.

Gas-liquid chromatography (GLC) if equisetin showed two components, the antibiotic and its degradation product. Conversion of antibiotic to a degradation product varied with temperature and residence time in the columns. Chromatographs from short columns (2 ft.) at 180° C. showed that the degradation peak represented only 3% of the sample. However at 190° C., this peak increased and accounted for 6–8% of the sample. Chromatographs from 6-ft. columns at 220° C. indicated that almost half the antibiotic was converted to the degradation product.

The elemental, IR, UV, and GLC analysis, along with the mass spectroscopic and nuclear magnetic resonance (NMR) studies, indicate that equisetin has the following structure:

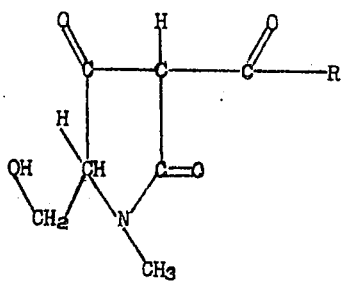

where $R = C_{15}H_{23}$ containing three $CH_3$- groups, two double bonds, and two ring formations.

The intraperitoneal $LD_{50}$ dose of equisetin by Weil's procedure [Biometrics 8: 249–252 (1952)] was 63.0 mg./kg. body weight with a 95% confidence interval of 50.1 to 79.3 mg./kg. Lethal action was slow. Although mice receiving 100 or 200 mg./kg. dosages were lethargic, death did not occur before the second day after treatment, and mortalities continued for 4 da. post-injection. Mice surviving 25- or 50-mg./kg. doses demonstrated no visible ill effects during 4 wk. of observation.

Seven strains each of *Bacillus subtilis* and *Staphylococcus aureus* and two of three *Mycobacterium phlei* strains were inhibited by 1 μg./ml. concentrations of equisetin (Table 1). *Nesseria perflava*, five strains, did not grow on the TGY agar containing from 1 to 4 μg./ml. equisetin. Other than *N. perflava*, none of the tested gram-negative bacteria or fungi was inhibited by equisetin levels up to 128 μg./ml.

A comparison of the minimum inhibitory concentrations (MIC) of equisetin with streptomycin and isoniazid for some gram-positive bacteria and *N. perflava* showed that a lower concentration of equisetin were required for the in vitro inhibition of the tested bacteria than was required for inhibition by streptomycin or isoniazid.

The following example is intended only to further illustrate the invention and is not to be construed as limiting the scope of the invention as defined by the claims.

EXAMPLE 1

Production and purification. NRRL 5537 was cultured in Fernbach flasks containing 200 g. of white corn grits moistened with 100 ml. water. Before autoclaving, 50 ml. of water were added and the remaining 50 ml. after the autoclaved grits were loosened with a stirring rod. Inoculum was prepared by incubating NRRL 5537 for 10–14 da. at room temperature on 2–3 g. of grits suspended in 5 ml. of 1.5% agar. Copious amounts of conidia are produced on the corn grit medium. Fermentation flasks were inoculated with 1 ml. of the loosened surface growth suspended in 8 ml. of water. During incubation (3–4 wk. at room temperature) the medium was shaken daily. The fermented grits were extracted by blending the contents of each flask twice in a Waring Blender jar for 1–2 min. with 1 liter of acetone. The acetone solution was separated from the grits by filtration. Acetone from the combined extracts was removed under vacuum, and the residual watery milieu (ca, 500 ml./kg. of substrate) containing the dissolved or suspended antibiotic was acidified to pH 2.0 with sulfuric acid. After acidification the suspension was partitioned into hexane; six 200-ml. volumes of hexane removed nearly all of the product. As the hexane evaporated at room temperature, a gellike matrix formed; with complete evaporation, 16–25 g. of a reddish solid product was obtained from a kilogram of white corn grits. The crude product was dissolved in 200 ml. boiling hexane and filtered. Red pigments re- Table 1

| NRRL No. | Bacterium | Antimicrobial agent MIC μg./ml. | | |
|---|---|---|---|---|
| | | Equisetin | Streptomycin | Isoniazid |
| B-609 | *Mycobacterium phlei* | 1.0 | 2.0 | 4.0 |
| B-610 | *M. phlei* | 1.0 | 2.0 | 4.0 |
| B-4051 | *M. phlei* | 2.0 | 2.0 | 4.0 |
| B-612 | *M. smegmatis* | 8.0 | 2.0 | 4.0 |
| B-2141 | *M. rhodochrus* | 0.5 | 2.0 | 64.0 |
| B-543 | *Bacillus subtilis* | 0.5 | 4.0 | 128[1] |
| B-558 | *B. subtilis* | 0.5 | 8.0 | — |
| B-644 | *B subtilis* | 0.5 | 2.0 | — |
| B-765 | *B. subtilis* | 0.5 | 2.0 | — |
| B-972 | *B. subtilis* | 0.5 | 8.0 | — |
| B-1650 | *B. subtilis* | 1.0 | 8.0 | — |
| B-3284 | *B. subtilis* | 1.0 | 4.0 | — |
| B-120 | *Staphylococcus aureus* | 1.0 | 2.0 | — |
| B-124 | *S. aureus* | 1.0 | 4.0 | — |
| B-313 | *S. aureus* | 0.5 | 2.0 | — |
| B-678 | *S. aureus* | 1.0 | 8.0 | — |
| B-1317 | *S. aureus* | 1.0 | 4.0 | — |
| B-1318 | *S. aureus* | 1.0 | 8.0 | — |
| B-2746 | *S. aureus* | 1.0 | 2.0 | — |
| B-1458 | *Neisseria perflava* | 2.0 | 2.0 | — |
| B-1788 | *N. perflava* | 2.0 | 2.0 | — |
| B-1789 | *N. perflava* | 4.0 | 2.0 | — |
| B-1790 | *N. perflava* | 1.0 | 2.0 | — |
| B-1791 | *N. perflava* | 4.0 | 4.0 | — |

[1] *B. subtilis*, *S. aureus*, and *N. perflava* strains were not inhibited by 128 μg. of isoniazid per ml. medium.

covered along with the antibiotic were removed from the hexane filtrate by washing 20–30 times with small volumes (2–3 ml.) of ethanol until pigment was no longer visible in the ethanol layer. The ethanol-pigment layer was removed from the hexane-antibiotic layer with a Pasteur pipette. After hexane evaporated, the primary recovery product was washed several times with 20–30 ml. volumes of hexane.

The ethanol-pigment layers were combined, evaporated, and extracted with boiling hexane for additional recovery of product. The hexane was cleared of red pigment by washing 12–15 times with 2–3 ml. portions of ethanol. The clear hexane layer was evaporated and the product washed several times with hexane. Repeated ethanol-pigment washings were recovered and partitioned into boiling hexane until a gel no longer formed upon evaporation of the hexane. Exhaustive partitioning of the ethanol-pigment washes into hexane yielded a pink powder, the secondary recovery product.

Antibiotic assay procedure. A standard curve was prepared by diluting chromatographically pure *F. equiseti* NRRL 5537 antibiotic in acetone and adding levels between 0.5 and 8 μg. to 12.7 mm. filter paper discs. The standard discs were placed on the surface of TGY agar [Haynes et al., Appl. Microbiol. 3: 361–368 (1955)], 6 ml. in a standard petri dish, inoculated with $1.5 \times 10^7$ *B. subtilis* NRRL B-3284 spores and incubating overnight at 37° C. The mean inhibition zone diameter of three discs for each concentration of antibiotic was plotted semilogarithmically and the mean response of each sample was calculated from the standard. The total amount of antibiotic produced per kilogram of grits was calculated from the potency and the combined volume of acetone and blended grits. Antibiotic remaining in the grits was estimated from the potency and difference in volume of acetone plus grits and the volume of acetone recovered from the second extraction. Antibiotic content of other preparations obtained during purification of the product was calculated from dilutions of weighed samples and their potencies.

Physical and chemical analyses. Thin layer chromatography was carried out on plates coated with Silica Gel G (0.5 mm.) and activated at 110° C. for 2 hr. The developing solvent was either toluene-methanol (7:3, v/v) or acetonitrile-water-benzene (90:6:4, v/v/v). Zones were detected by spraying developed plates with p-anisaldehyde (0.5 ml. in 85 ml. methanol, 10 ml. glacial acetic acid, and 5 ml. concentrated sulfuric acid) and then heating at 110° C. for 5–10 min. [Scott et al., Appl. Microbiol. 20: 839–842 (1970)]. Either iodine vapor or concentrated sulfuric acid was also used to detect possible impurities.

Melting points (uncorrected) were determined with a Fisher-Johns apparatus. Infrared spectra were obtained on a Beckman Model 1R-8 spectrophotometer from films deposited on KRS-5 plates (Wilks, Inc.) or from solutions in a 1-mm. sodium chloride cell. Mass spectra were obtained on a Nuclide high-resolution instrument Model 12-90G. Ultraviolet spectra were recorded from a Beckman DG-G with the absolute ethanol solutions of antibiotic at 25 μg./ml. Elemental analysis was carried out in a Perkin-Elmer CHN analyzer 240. Solubilities were measured by the procedure of Shriner et al. [*The Systematic Identification of Organic Compounds. A Laboratory Manual*, John Wiley and Sons., Inc., New York].

Copper salt of the antibiotic was prepared [Rosset et al., Biochem. J. 67: 390–400 (1957)] and crystallized from methanol-water as clusters of fine green needles. The copper content was determined on a Perkin-Elmer 303 atomic absorption spectrophotometer.

Gas-liquid chromatography of *F. equiseti* NRRL 5537 preparations was carried out on a Bendix Model 2500 chromatograph equipped with on-column flame ionization detectors. Retention times of the antibiotic and its degradation product were determined on glass columns (2 ft. × 2 mm. and 6 ft. × 2 mm.) packed with SE-30 (3%) on Supelcon AW-DMCS (Supelco, Inc.). Operating parameters were: temperature, 180° or 190° C. isothermally for 2-ft. columns and programmed from 180° to 220° C. at 5° C./min. for 6-ft. columns; carrier gas, nitrogen (40 ml./min.); hydrogen (20 ml./min.); air (400 ml./min.); injection ports and detectors, 250° C. Samples were dissolved in absolute ethanol (10 mg./ml.), and 2 μl. were used for analyses. Peak areas and retention times were obtained with a Hewlett/Packard Model 3370 B integrator.

Animal toxicity. Chromatographically pure antibiotic was dissolved in warm propylene glycol and injected intraperitoneally into 25 g. Swiss-Webster female mice. The $LD_{50}$ dose was calculated by Weil's procedure (supra) with the following notation: $K = 3$; $n = 6$; $r = 0$, 1, 6, 6; $d = 0.3010$; and $Da = 25$ mg./kg. body weight.

Minimum inhibitory concentrations for microorganisms. The *F. equiseti* NRRL 5537 antibiotic was diluted in ethanol. Streptomycin sulfate and isoniazid were diluted in water. Amounts up to 1 ml. were added to TGY agar to provide the desired double dilution test concentrations. Minimum inhibitory concentrations of the antimicrobial agents were determined by streaking a loopful of standardized suspensions of 24- to 48-hr. cultures of selected microorganisms onto the surface of 20 ml. of the modified TGY agar in a standard petri dish. Microorganisms were cultured on TGY agar slants and diluted with TGY broth to yield a transmittance of about 90% at 600 nm. in a Spectronic-20 spectrophotometer. All cultures grew on control plates containing 1 ml. ethanol per 100 ml. TGY agar. Bacteria were incubated at 37° C. and the fungi at room temperature. Cultures were observed after 24 and 48 hr., and the MIC was recorded as that concentration of antibiotic which completely inhibited growth.

Figure 2:
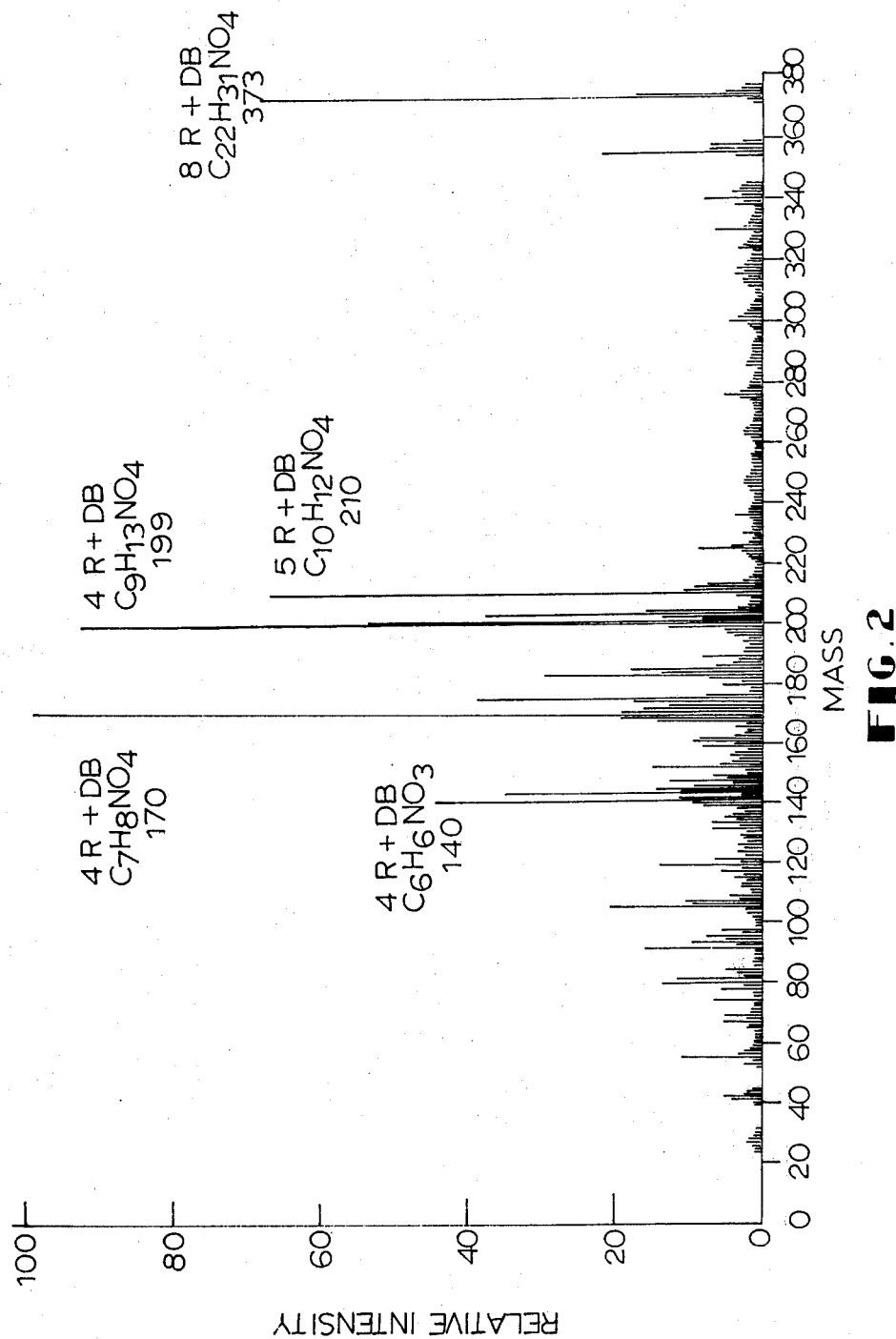

I claim:
1. An antibiotic, equisetin, having the following structure:

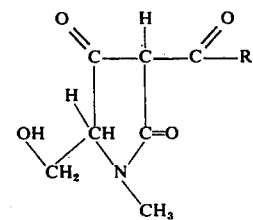

where R has the emperical formula $C_{15}H_{23}$ and contains three $CH_3$- groups, two double bonds, and two ring formations; said equisetin being further characterized by the following properties:
 a. a nonfluorescent white amorphous powder;
 b. the ultraviolet spectrum of FIG. 1;
 c. the mass spectrograph of FIG. 2;
 d. the infrared spectrum of FIG. 3;
 e. a melting point range of 65° to 66° C.;
 f. a solubility in acetone of 660 mg./ml., in ethanol of 330 mg./ml., in methanol of 220 mg./ml., in hexane of 0.8 mg./ml., and in water of 0.3 mg./ml.;
 g. a molecular weight of 373 g./mole;

h. $R_F$ values of thin layer chromatography using silica gel and the following solvent systems:

acetonitrile:water:benzene (90:6:4, v/v/v)  $R_F$ 0.53
toluene:methanol (7:3, v/v)  $R_F$ 0.61;

i. a positive ferric chloride test; and
j. the following elemental analysis: C, 70.95; H, 8.39; N, 3.14; O, 17.52 (by difference).

2. A process for the production of the antibiotic equisetin comprising cultivating *Fusarium equiseti* NRRL 5537 in contact with a nutrient medium until the antibiotic equisetin has been produced and isolating said equisetin from the fermentation media.

3. A process for the production of the antibiotic equisetin as described in claim 2 wherein the cultivation is carried out on moist white corn grits, moist cracked corn, moist pearled wheat, or moist rolled oats.

4. A process for the production of the antibiotic equisetin as described in claim 3 wherein the cultivation is carried out on moist corn grits.

* * * * *